United States Patent [19]

Wenig et al.

[11] Patent Number: 4,778,810

[45] Date of Patent: Oct. 18, 1988

[54] NASAL DELIVERY OF CAFFEINE

[75] Inventors: Jeffrey Wenig; Devin N. Wenig, both of Dix Hills, N.Y.

[73] Assignee: Nastech Pharmaceutical Co., Inc., Hauppauge, N.Y.

[21] Appl. No.: 1,340

[22] Filed: Jan. 8, 1987

[51] Int. Cl.⁴ ............................................. A61K 31/52
[52] U.S. Cl. ..................................................... 514/263
[58] Field of Search ......................................... 514/263

[56] References Cited

PUBLICATIONS

Chem. Abst., vol. 99—200, 503X (1983).

*Primary Examiner*—Stanley J. Friedman
*Attorney, Agent, or Firm*—Wyatt, Gerber, Burke and Badie

[57] ABSTRACT

Nasal compositions useful for the delivery of caffeine alone or with other therapeutic agents.

8 Claims, No Drawings

NASAL DELIVERY OF CAFFEINE

This invention is concerned with nasal administration of caffeine in nasal compositions containing caffeine as the sole therapeutic agent or as one of two or more physiologically active agents. It is concerned also with a nasal method of delivering caffeine to a mammalian subject in need of such treatment.

Caffeine is a central stimulant the therapeutic activity of which has been well documented and need not be discussed in detail. It has been utilized alone and in various therapeutic mixtures containing other physiologically active compounds, for example analgesic agents.

The term "caffeine" as used herein is intended to encompass not only caffeine as the anhydrous powder, but any salt or derivative of caffeine having caffeine like activity which is non-toxic and pharmaceutically acceptable. See, for example, The Merck Index, ninth edition, Merck & Co., Inc. Rahway, N.J. (1976), pp. 207–208, for a description of caffeine salts, derivatives and mixtures which may prove useful in the compositions of the present invention. Nevertheless, caffeine as the anhydrous powder base is presently preferred and, where specific amounts of caffeine are set forth below, such amounts are given in mg of the anhydrous base.

A large number of pharmaceutical compositions containing caffeine together with a pharmaceutically acceptable carrier have been described. U.S. Pat. No. 1,298,670 describes chewing gum compositions containing caffeine. The use of caffeine in various pharmaceutical carriers and in foods is described in U.S. Pat. No. 3,864,489. Sunshine et al in U.S. Pat. No. 4,464,376 describes pharmaceutical mixtures containing caffeine together with non-narcotic/non-steroidal anti-inflammatory agents, a narcotic analgesic or both. None of these patents specifically describe nasal compositions or their use.

Caffeine is usually administered in oral formulations in tablets, capsules, elixers, suspensions or syrups. However such oral formulations are not rapidly absorbed from the intestinal track and, often do not produce desirably high blood levels in a short time. Some of the desired product may be wasted by excretion before it is absorbed. Moreover, caffeine is known to be an irritant of the stomach mucosa.

Injectable solutions and suspensions although rarely used with caffeine might be more satisfactory for producing rapid high blood levels. However, such compositions must normally be administered under the supervision of trained medical personnel in a doctor's office or out-patient department. Many people strongly object to injections.

It has been discovered that caffeine containing compositions can be usefully administered to mammals in novel nasal compositions at low dosage levels to elicit a systemic therapeutic response and to provide enhanced bioavailability, minimized variations in blood levels, more rapid onset of activity, ease of administration, and reduced side effects compared to most current methods of administration. The nasal administration process of this invention is significantly more efficient than oral or parenteral administration. Simple, small containers such as eye droppers, aerosol or other pressurized containers, and tubes which can be easily carried in a pocket or purse can be used for delivery. Caffeine is often used as a stimulant to prevent sleep, particularly by auto and truck operators. Rapid onset of activity is obviously important for such use.

Nasal delivery of therapeutic agents has been well known for a number of years. See, for example, U.S. Pat. Nos. 4,428,883; 4,284,648 and 4,394,390; and PCT application International Publication No. WO83/00286. See also, Hussain et al, *J. Pharm. Sci.*: 68, No. 8, 1196 (1979); 69 1240 (1980) and 69 (1980).

While nasal administration of certain therapeutic agents to mammals, especially humans is known, it is not a necessary conclusion from such knowledge that all therapeutic agents can be usefully administered by this route. In fact it has been shown that many drugs cannot be usefully administered by the nasal route. It certainly is not a suggestion that the compounds of this invention can be usefully administered nasally to achieve enhanced bioavailability and sustained therapeutic blood levels.

Zatuchinin, et al, for example reported in LHRH Peptides as Female and Male Contraceptives, Harper & Row, Publishers (1976) that although LHRH peptides were effective when administered intranasally, a much higher dose was required than with parenteral administration.

Childrey and Essex reported an immediate and marked pressor response upon injection of 1 mg of nicotine in dogs, but little or no effect on injections of the same or larger amounts into the sinus of dogs or cats. Arch. Otolaryngol., 14 564 (1931).

Hussain et al have concluded that peptides are poorly absorbed through the nasal mucosa. See Transnasal Systemic Medications, Edited by Y. W. Chien, Elsevier Science Publishers, 1985, page 121 et seq, at page 122.

This invention provides caffeine containing compositions including gels, sprays and solutions which may be administered in the form of drops all of which are specifically formulated for nasal administration to permit therapeutic delivery of effective amounts of caffeine through the nasal mucous membrane.

More specifically the compositions of the invention are for nasal administration and contain a therapeutically effective amount of caffeine. They are conveniently provided as isotonic aqueous solutions, suspensions or viscous compositions which may be buffered to a selected pH. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. The preferred compositions have a viscosity of 2500 to 5000 cps, since above that range they become more difficult to administer.

Liquid sprays and drops are normally easier to prepare than gels and other viscous compositions. Additionally, they are somewhat more convenient to administer, especially in multi-dose situations. Viscous compositions, on the other hand are much preferred in the practice of this invention since they can be formulated within the appropriate viscosity range to provide longer contact periods with the nasal mucosa and reduce the amount of caffeine per dosage unit necessary to achieve the desired result.

The caffeine of the invention will be most efficiently absorbed through the nasal membranes if the pH is from 4 to 6. However the pH of the compositions may vary from about 3 to 7. The pH is suitably maintained with a physiologically acceptable buffer, suitably an acetate, phosphate, phthalate or borate buffer. Acetate buffers are preferred for convenience and economy.

The concentration of caffeine may vary appreciably with the condition being treated, the age and size of the patient and other factors readily evaluated by the physician or veterenarian in attendance. Therapeutically effective amounts of caffeine may vary appreciably if other physiologically active agents are present. However, as a generalization, the compositions of the invention in bulk or unit dosgae form will typically contain the selected agent as a concentration of from about 25 to 2000 mg/ml. Typically, the volume of a dosage unit is from about 0.05 to 0.3 ml.

The desired isotonicity of the composition may be accomplished using sodium chloride, or other pharmaceutically acceptable agent such as dextrose, boric acid, sodium tartrate, propylene glycol or other inorganic or organic solute. Sodium chloride is preferred particularly for buffers containing sodium ions.

Viscosity of the compositions may be maintained at the selected level using a therapeutically acceptable thickening agent. Methyl cellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

Preferred compositions within the scope of this invention will contain a humectant to inhibit drying of the mucous membrane and to prevent irritation. Any of a variety of therapeutically acceptable humectants can be employed including, for example sorbitonl propylene glycol or glycerol. As with the thickeners, the concentration will vary with the selected agent, although the presence of absence of these agents, or their concentration is not an essential feature of the invention.

Enhanced absorption across the nasal membrane can be accomplished employing a therapeutically acceptable surfactant. Typically useful surfactants for these therapeutic compositions include polyoxyethylene derivatives of fatty acid partial esters of sorbitol anhydrides such as Tween 80, Polyoxyl 40 Stearate, Polyoxyethylene 50 Stearate and Octoxynol. The usual concentration is from 1% to 10% based on the total weight.

A therapeutically acceptable preservative is generally employed to increase the shelf life of the compositions. Benzyl alcohol is suitable, although a variety of preservatives including, for example, Parabens, thimerosal, chlorobutanol, or benzalkonium chloride may also be employed. A suitable concentration of the preservative will be from 0.02% to 2% based on the total weight, although there may be appreciable variation depending upon the agent selected.

Those skilled in the art will recognize that the components of the compositions must be selected to be chemically inert with respect to the active agent. This will present no problem to those skilled in chemical and pharmaceutical principles, or problems can be readily avoided by reference to standard texts or by simple experiments.

The compositions of this invention may contain other therapeutically active agents together with the caffeine. These may include, for example, analgesics, anti-inflammatory and antipyretic agents such as aspirin, acetaminophen, phenacetin or other therapeutic agents normally employed with caffeine. When the compositions are intended for pain killing they may contain codeine, propoxyphene, oxycodone or other narcotic analgesics. Other useful combined therapeutics include those described in the above identified patent to Sunshine et al. These include, for example, non-steroidal anti-inflammatory drugs such as naproxen, fenoprofen, indoprofen, diflunisal, indomethacin or mefammic acid. As pointed out in the aforesaid patent, the caffeine enhances the activity of the anti-inflammatory drug. As will be observed from the examples, caffeine is not necessarily the principal therapeutically active agent in the compositions of the invention.

The therapeutically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent.

Typical compositions of this invention contain the following components per 100 ml:

| | |
|---|---|
| Benzyl alcohol, NF | 1.50 ml |
| Sodium chloride, NSP | q.s. |
| Methyl cellulose, USP (400 cps) | 2.00 gm |
| Acetic acid, NF | q.s. |
| Sodium acetate (anhyd, USP) | q.s. |
| Sorbitol soln., USP | 5.00 ml |
| Caffeine | 1-20 gm |
| Water, purified q.s. | 100 ml | pH and tonicity will be adjusted q.s. to assure maximum adsorption and minimal local irritation. They will depend on such factors as concentration of the caffeine and the form in which it is employed, e.g. free base, salt, hydrate, etc.

The following non-limiting examples are given by way of illustration only and are not to be considered limitations of this invention, many apparent variations of which are possible without departing from the spirit or scope thereof.

EXAMPLE 1

The following compositions are prepared by mixing the named components.

| | |
|---|---|
| A | |
| Phenylmercuric Acetate NF | 0.002 g |
| Boric Acid NF | q.s. |
| Methylcellulose (4000 CPS) USP | 2.000 g |
| Acetic acid NF | q.s. |
| Sodium Acetate (Anhydrous) USP | q.s. |
| Glycerin USP | 5.000 ml |
| Caffeine | 2.0 g |
| Water, purified USP q.s. | 100.000 ml |
| B | |
| Benzalkonium Chloride NF | 0.020 g |
| Potassium Chloride USP | q.s. |
| Hydroxyethyl Cellulose (3500-4000 CPS) NF | 1.000 g |
| Acetic Acid NF | q.s. |
| Sodium Acetate (Anhydrous) USP | q.s. |
| Propylene Glycol USP | 5.000 ml |
| Caffeine | 20.0 g |
| Water, Purified USP q.s. | 100.000 ml |
| C | |
| Thimerosal USP | 0.002 g |
| Dextrose USP | q.s. |

|  |  |
|---|---|
| *-continued* | |
| Polysorbate 80 USP | 10.000 g |
| Methylcellulose (4000 CPS) USP | 1.33 g |
| Acetic Acid NF | q.s. |
| Sodium Acetate (Anhydrous) USP | q.s. |
| Glycerin USP | 5.000 ml |
| Caffeine | 5.0 g |
| Water, Purified q.s. | 100.000 ml |
| D | |
| Methylparaben NF | 0.020 g |
| Propylparaben NF | 0.010 g |
| Sodium Chloride USP | 0.820 g |
| Xanthan Gum NF | 2.000 g |
| Acetic Acid NF | 0.100 g |
| Sodium Acetate (Anhydrous) USP | 0.270 g |
| Propylene Glycol USP | 5.000 g |
| Caffeine | 2.0 g |
| Water, Purified q.s. | 100.000 ml |
| E | |
| Thimerosal USP | 0.002 g |
| Dextrose USP | q.s. |
| Polysorbate 80 USP | 10.000 g |
| Methylcellulose (4000 CPS) USP | 1.33 g |
| Acetic Acid NF | q.s. |
| Sodium Acetate (Anhydrous) USP | q.s. |
| Glycerin USP | 5.000 ml |
| Caffeine | 2.0 g |
| Aspirin | 5.0 g |
| Water, Purified q.s. | 100.000 ml |
| F | |
| Methylparaben NF | 0.020 g |
| Propylparaben NF | 0.010 g |
| Sodium Chloride USP | 0.820 g |
| Xanthan Gum NF | 2.000 g |
| Acetic Acid NF | 0.100 g |
| Sodium Acetate (Anhydrous) USP | 0.270 g |
| Propylene Glycol USP | 5.000 g |
| Caffeine | 4.0 g |
| Codeine | 1.0 g |
| Water, Purified q.s. | 100.000 ml |
| G | |
| Thimerosal USP | 0.002 g |
| Dextrose USP | q.s. |
| Polysorbate 80 USP | 10.000 g |
| Methylcellulose (4000 CPS) USP | 1.33 g |
| Acetic Acid NF | q.s. |
| Sodium Acetate (Anhydrous) USP | q.s. |
| Glycerin USP | 5.000 ml |
| Caffeine | 1.0 g |
| Aspirin | 3 g |
| Acetaminophen | 1.5 g |
| Salicylamide | 2. g |
| H | |
| Methylparaben NF | 0.020 g |
| Propylparaben NF | 0.010 g |
| Sodium Chloride USP | 0.820 g |
| Xanthan Gum NF | 2.000 g |
| Acetic Acid NF | 0.100 g |
| Sodium Acetate (Anhydrous) USP | 5.000 g |
| Caffeine | 2.0 g |
| Indomethicin | 1.0 g |
| Water, Purified q.s. | 100.000 ml |

The viscosities of all of the above compositions are within the viscosity range defined above. Solutions are prepared by omitting the thickening agents.

What is claimed is:

1. A method of treating a mammal in need of a central stimulatory response with caffeine which comprises nasal administration of a composition containing, as the only therapeutically active ingredient, an amount of caffeine which is effective to elicit a systemic, therapeutic, central stimulatory response, said caffeine being in an isotonic aqueous buffer at a pH of from about 3 to 7.

2. A method as in claim 1 wherein the composition contains a sufficient amount of a therapeutically acceptable thickening agent so that the viscosity is from about 2500 to 6500 cps.

3. A method of treating a mammal in need of a central stimulatory response with caffeine which comprises nasal administration of a composition in dosage unit form containing, as the only therapeutically active ingredient, from 25 to 2000 mg/ml of caffeine in an isotonic aqueous buffer at a pH of from about 3 to 7.

4. A method as in claim 3 wherein the composition contains a sufficient amount of a therapeutically acceptable thickening agent so that the viscosity is from about 2500 to 6500 cps.

5. A therapeutic composition for nasal administration containing as the only therapeutically active ingredient an amount of caffeine which is effective to elicit a systemic, therapeutic, central stimulatory response, said caffeine being in an isotonic aqueous buffer at a pH of from about 3 to 7.

6. A therapeutic composition of claim 5 containing a sufficient amount of a therapeutically acceptable thickening agent so that the viscosity is from about 2500 to 6500 cps.

7. A therapeutic composition for nasal administration in dosage unit form containing from 25 to 2000 mg/ml of caffeine as the only therapeutically active ingredient in an isotonic aqueous buffer at a pH of from about 3 to 7.

8. A therapeutic composition of claim 7 containing a sufficient amount of a therapeutically acceptable thickening agent so that the viscosity is from about 2500 to 6500 cps.

* * * * *